United States Patent [19]
Satherley

[11] Patent Number: 6,077,223
[45] Date of Patent: Jun. 20, 2000

[54] AMBULATORY RECORDER HAVING CONTROL SCREEN TO PRESENT DUAL INTERFACE FOR DUAL USERS

[75] Inventor: Richard J. Satherley, Felbridge, United Kingdom

[73] Assignee: Medtronic, Inc., Minneapolis, Minn.

[21] Appl. No.: 09/129,915

[22] Filed: Aug. 6, 1998

[51] Int. Cl.⁷ .................................................. A61B 5/00
[52] U.S. Cl. ........................ 600/309; 600/300; 600/361
[58] Field of Search ..................................... 600/300, 301, 600/389, 390, 309, 361; 128/920, 921; 369/75.1; 206/470; 361/680, 681, 682; 364/708.1

[56] References Cited

U.S. PATENT DOCUMENTS

| | | |
|---|---|---|
| D. 396,037 | 7/1998 | Cappa et al. . |
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. . |
| 5,010,888 | 4/1991 | Jadvar et al. . |
| 5,012,411 | 4/1991 | Policastro et al. . |
| 5,016,636 | 5/1991 | Kulakowski . |
| 5,042,481 | 8/1991 | Suziki et al. . |
| 5,072,458 | 12/1991 | Suzuki . |
| 5,086,778 | 2/1992 | Mueller et al. . |

(List continued on next page.)

FOREIGN PATENT DOCUMENTS 0 356 603  9/1988  Sweden .

Primary Examiner—Eric F. Winakur
Attorney, Agent, or Firm—Thomas F. Woods; Michael J. Jaro; Harold Patton

[57] ABSTRACT

An ambulatory data recorder having a selectable device control interface. The selectable device control interface permitting a selection to be made between a first device control interface, in which the full device control set is accessible, and a second control interface, in which only a partial amount of the device control set is accessible. Typically the first control interface is intended for use by physicians and the second control interface is intended for use by patients. The selectable device control interface is provided by a combination of device controls and a moveable device cover. The cover moveable from a first opened position in which the full device control set is accessible and a second closed position in which only a partial amount of the device control set is accessible. Preferably the cover permits operation of at least one of the device controls regardless of its position. The cover further, however, preferably masks the labels on the at least one of the device controls to simplify operation by the patient. Moreover, the cover is further preferably mounted on a breakaway hinge and is moveable into the opened position only through a tool.

22 Claims, 5 Drawing Sheets

U.S. PATENT DOCUMENTS

| | | |
|---|---|---|
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |
| 5,131,816 | 7/1992 | Brown et al. . |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |
| 5,226,431 | 7/1993 | Bible et al. . |
| 5,228,450 | 7/1993 | Sellers . |
| 5,238,001 | 8/1993 | Gallant et al. . |
| 5,261,401 | 11/1993 | Baker et al. . |
| 5,263,491 | 11/1993 | Thornton . |
| 5,273,033 | 12/1993 | Hoffman . |
| 5,292,344 | 3/1994 | Douglas . |
| 5,305,202 | 4/1994 | Gallant et al. . |
| 5,305,761 | 4/1994 | Byrne et al. . |
| 5,307,263 | 4/1994 | Brown . |
| 5,309,920 | 5/1994 | Gallant et al. . |
| 5,338,157 | 8/1994 | Blomquist . |
| 5,341,291 | 8/1994 | Roizen et al. . |
| 5,343,870 | 9/1994 | Gallant et al. . |
| 5,355,892 | 10/1994 | Saltzstein . |
| 5,365,499 | 11/1994 | Sell ......................................... 368/262 |
| 5,368,562 | 11/1994 | Blomquist et al. . |
| 5,381,351 | 1/1995 | Kwong et al. . |
| 5,388,587 | 2/1995 | Knutsson et al. . |
| 5,411,022 | 5/1995 | McCue et al. . |
| 5,429,602 | 7/1995 | Hauser . |
| 5,431,634 | 7/1995 | Brown . |
| 5,432,698 | 7/1995 | Fujita . |
| 5,438,985 | 8/1995 | Essen-Moller . |
| 5,479,019 | 12/1995 | Gross . |
| 5,479,935 | 1/1996 | Essen-Moller . |
| 5,482,446 | 1/1996 | Williamson et al. ................... 604/153 |
| 5,507,904 | 4/1996 | Fisher et al. . |
| 5,526,809 | 6/1996 | Fiddian-Green . |
| 5,545,183 | 8/1996 | Altman . |
| 5,607,460 | 3/1997 | Kroll . |
| 5,645,068 | 7/1997 | Mezack et al. . |
| 5,657,759 | 8/1997 | Essen-Moller . |
| 5,701,894 | 12/1997 | Cherry et al. . |
| 5,704,368 | 1/1998 | Asano et al. . |
| 5,704,890 | 1/1998 | Bliss et al. . |
| 5,749,907 | 5/1998 | Mann . |
| 5,796,575 | 8/1998 | Podwalny et al. ...................... 361/681 | ic signal

AMBULATORY RECORDER HAVING CONTROL SCREEN TO PRESENT DUAL INTERFACE FOR DUAL USERS

FIELD OF THE INVENTION

The present invention relates to an ambulatory recorder, for medical and especially for diagnostic purposes, by means of a portable recorder, including providing the recorder with controls which present a dual interface for dual users.

Ambulatory recording and recorders are widely used. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram), EEG (Electroencephalogram) or pH and pressure (Motility) in the gastrointestinal tract. Preferably such a recorder should be able to record among a programmable number of channels at a variety of programmable frequencies.

One problem often faced with designing ambulatory recorders lies in the different types of people who are expected to use and thus interface with the device. Ambulatory recorders are typically used by both the physician as well as the patient from which the data is recorded. Each user has differing degrees of device-related sophistication. For data is recorded. Each user has differing degrees of device-related sophistication For physicians and other health care professionals, all the various sophisticated features of the device should be readily available. For the patients, only those features which the patient actually needs access to should be available.

SUMMARY OF THE INVENTION

An ambulatory data recorder having a selectable device control interface. The selectable device control interface permitting a selection to be made between a first device control interface, in which the full device control set is accessible, and a second control interface, in which only a partial amount of the device control set is accessible. Typically the first control interface is intended for use by physicians and the second control interface is intended for use by patients. The selectable device control interface is provided by a combination of device controls and a moveable device cover. The cover moveable from a first opened position in which the full device control set is accessible and a second closed position in which only a partial amount of the device control set is accessible. Preferably the cover permits operation of at least one of the device controls regardless of its position. The cover further, however, preferably masks the labels on the at least one of the device controls to simplify operation by the patient. Moreover, the cover is further preferably mounted on a breakaway hinge and is moveable into the opened position only through a tool.

The FIGS. are not necessarily to scale.

DETAILED DESCRIPTION OF THE DRAWINGS

Figure 1A:
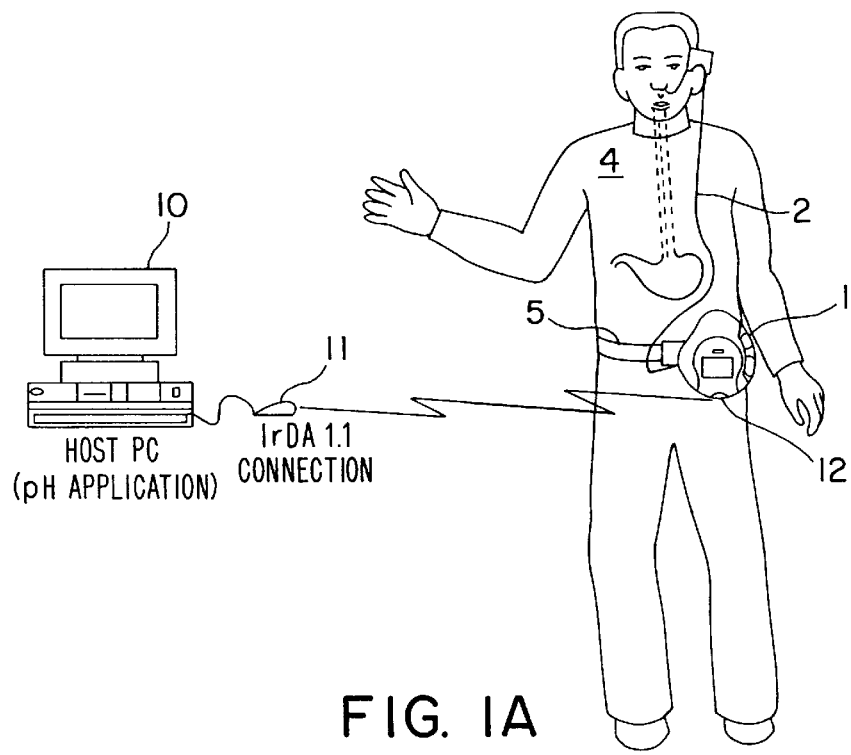
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back of the recorder enclosure which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body, from which data is to be sensed, including the esophagus, as depicted in this FIG. It should be noted, the ambulatory recorder of the present invention may be used to collect many or various types of data including gastrointestinal (including pH and pressure), neurological, as well as neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder further permits two separate sensors to be coupled to the device, as seen in FIG. 1B.

As further seen in this figure, the recorder may also communicate with a host PC 10 via an infra red data link facility through an IrDA connection 11, for example, a JETEYE ESI-57680 available form Extended Systems, Inc., Boise, Id., which connects with the recorder using the infra Red Data Association 1.1 Connection Protocol. As seen, infra red data connection makes a link to infra red port 12 on recorder.

Figure 1B:
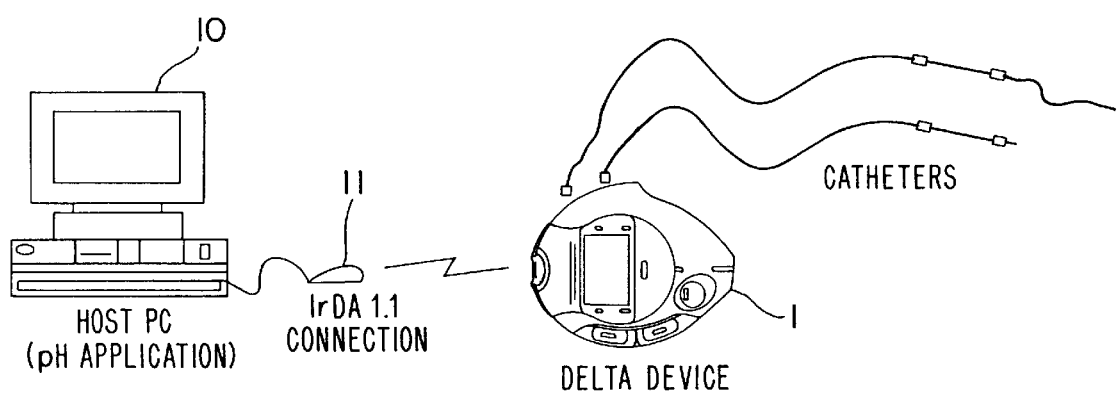
FIG. 1B illustrates a further manner in which the recorder 1 may also have an infra red data communication link made with a host PC.

FIG. 1B illustrates a further manner in which the recorder 1 may also have an infra red data communication link made with a host PC. In particular, the infra red data communication data recorder may be further made when the recorder is not worn by the patient. As discussed in more detail below, one of the advantages of the present invention is that the infra red data components and recorder case permits such a link to be made when the device is worn as shown in FIG. 1A as well as if the device is merely removed from the patient and positioned in proximity to mouse 11.

Figure 2:
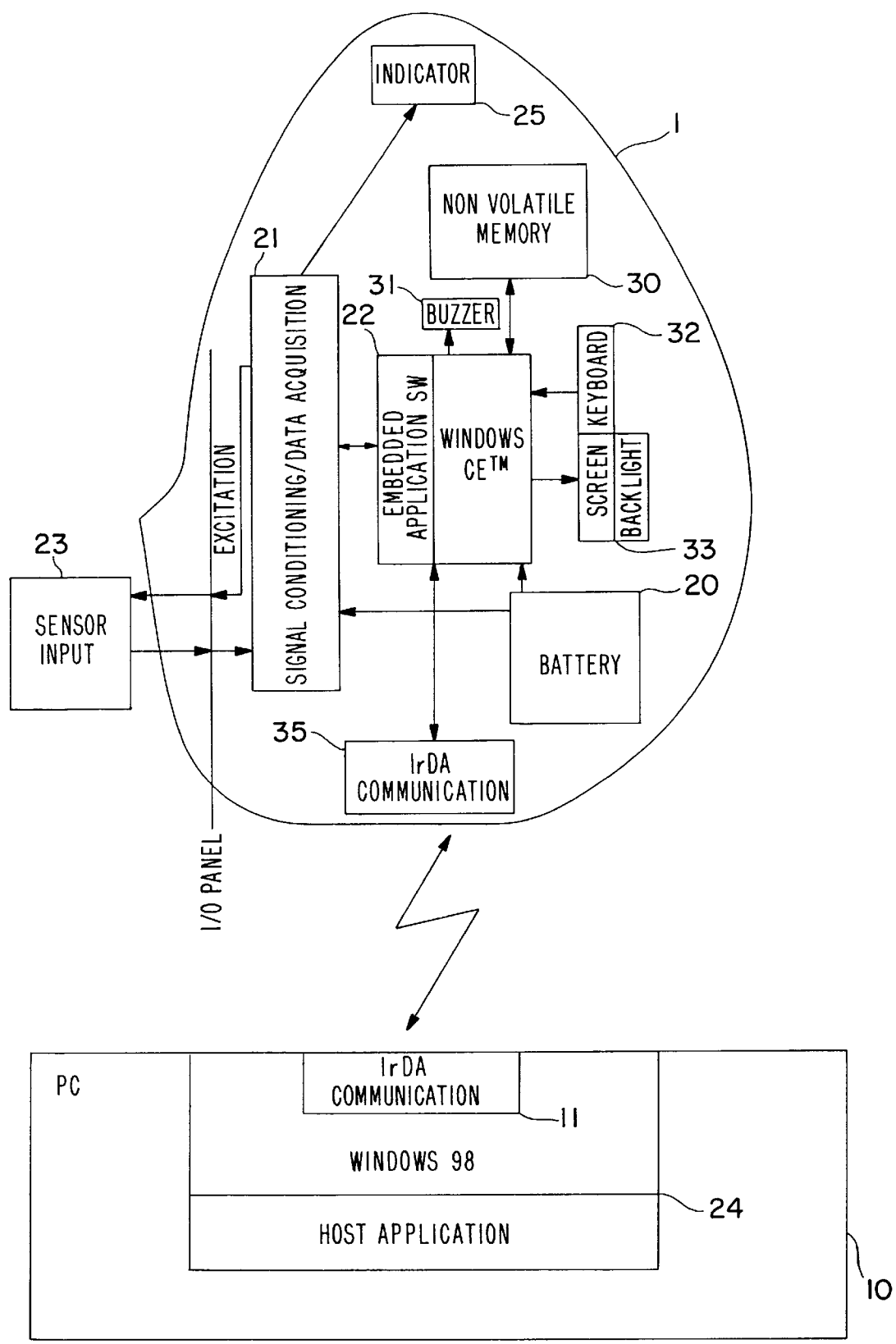
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning/data acquisition block that is driven by a real time processor 21, the battery is coupled as well as to a non-real time processor 22 that runs the application. As disclosed in more detail below, real time processor 21 is a lower power processor which is used to sample data which is received from sensor input 23 by a sensor attached thereto (not shown in this FIG.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In the preferred embodiment the real time processor is the model PIC16LC67 from Microchip Technology Inc., Chandler, Ariz.; the non real time processor is the model ElanSC400 from Advanced Micro Devices, Inc. Sunnyvale, Calif.; and non-volatile memory is the model Minicard AMMCL004AWP from Advanced Micro Devices, Inc. Sunnyvale, Calif.

Figure 3:
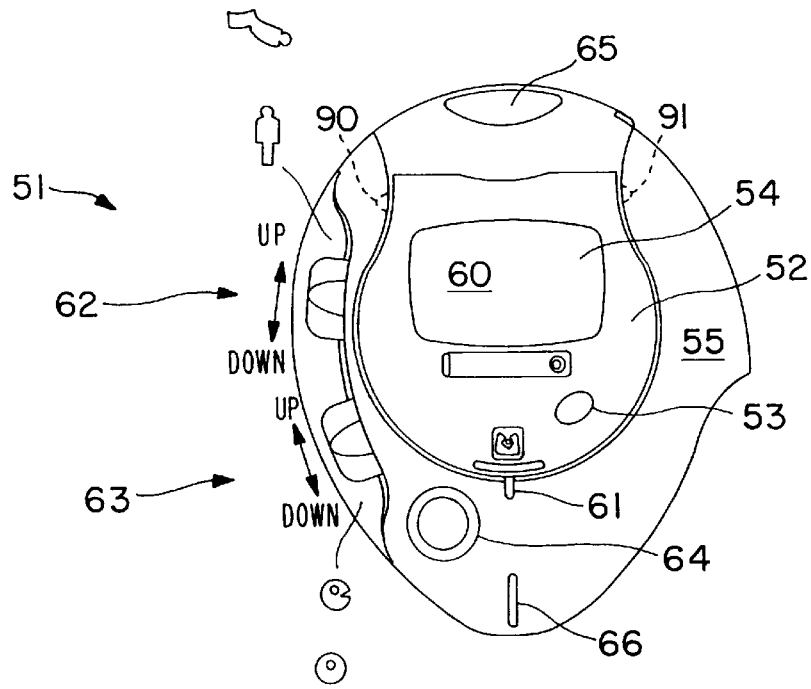
FIG. 3 is a front view of recorder according to the present invention.

FIG. 3 is a front view of recorder according to the present invention. In this view, recorder 51 has its movable front cover 52 closed. As discussed in more detail below, front cover further includes a movable push button shield 53 which allows access to one of the push button controls covered by the cover while in the down position. Shield, although allowing access to push button, obscures any notation of push button from the viewer when the cover is closed such that a very simplified control interface is presented to any user when the cover 52 is closed. Cover, while mainly opaque, also features a transparent window 54 to permit viewing of the LCD screen 60 which is integral with recorder (further depicted in FIG. 2). As seen window is positioned along cover so as to permit screen to be seen even while cover is closed. As mentioned, cover may be moved from a closed position, shown in this figure, to an open position, shown in FIG. 4. Movement is controlled by a cover catch 61, described in more detail in FIG. 9.

As seen, recorder also features a pair of period switches 62 and 63 which are movable in a linear fashion from a first to a second position. In the preferred embodiment, period switch 62 is a body position switch and the up position is used to mark periods when the patient is lying down or in a supine position. The down position is used to mark periods when the patient is standing or sitting upright. Period switch 63 preferably is a meal switch and the up position is used to mark a meal period while the down position is used for periods when the patient is not eating. The device further features, in its design, an event button 64 which the patient presses to mark events. Such events may include heart palpitations or reflux. Clock button 53, period switches 62 and 63 and event button 64 are all coupled to the keyboard function 32, shown in FIG. 2.

As seen, the device further features an infra red data output port having a two plane infra red lens 65. This feature is coupled to the infra red communication block 35 depicted in FIG. 2 and permits the device to communicate, through an infra red connection, to a host PC. The device also features an operation indicator light 66 which would indicate device operation.

Figure 4:
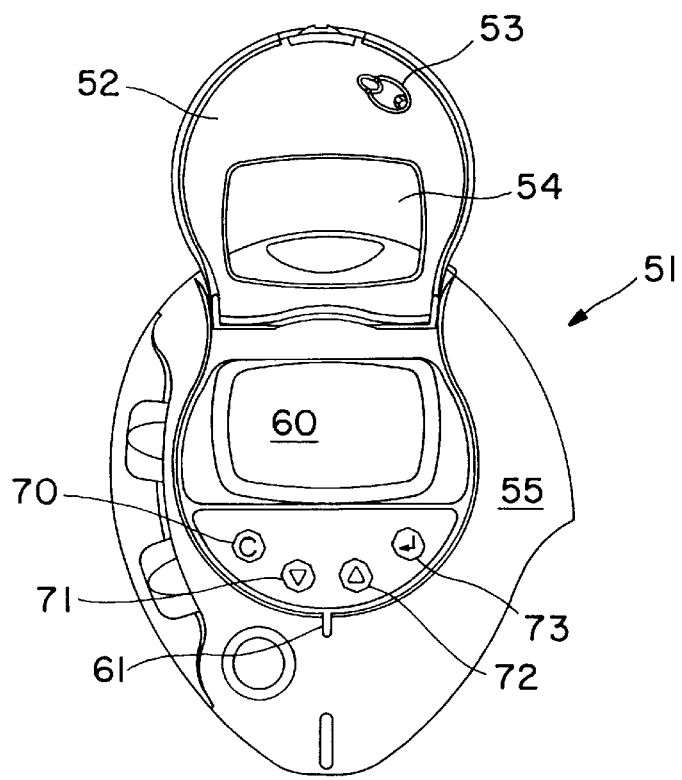
FIG. 4 is a front view of the recorder 51 in which the cover 52 has been raised and the device is open.

FIG. 4 is a front view of the recorder 51 in which the cover 52 has been raised and the device is open. As seen, when open, a series of controls 70, 71, 72 and 73 are exposed. As seen, control 70 is a push button and features, at its front face, the mark C. This control permits the user to return to the previous screen shown on display 60 without having to save any changes. Control 71 is a push button which, in the preferred embodiment, moves the selection bar shown in 60 to the next item down. Control 72 is a push button which, in the preferred embodiment, moves the selection bar to the next item up. Control 73 is, preferably, a push button which executes the current selection in the preferred embodiment.

As seen by a comparison of FIG. 3 and FIG. 4, control push button 73 may be operated regardless of whether the cover is opened or closed during the provision of movable push button 53. An important feature of this shield, however, is that it presents a different notation for the push button when the cover is closed as compared to when the cover is open. As discussed above, past ambulatory recorders have performed less than satisfactorily because too many controls were presented to the patient. While such controls are necessary to be presented to the physician so that the device may be programmed and its operating parameters set in an acceptable manner, such controls are not necessary for the patient when the device is merely recording. Thus, the movable pounds) is provided to the cover when open it will release from its hinge points without breaking such that it may thereafter be reinserted into its hinge. The breakaway feature is provided in a known manner, a deformable polymer cover along with removable hinges, e.g. interlocking hemispherical hinge points and recesses. Break-away hinge is provided through the engagement of a pair of oppositely disposed pins 90 and 91 (shown here as a dotted line) integral with cover 52 which engage into enclosure 55 and, thus, permit cover to be rotated from an open to a close position and vice versa. Break-away capability is provided because the pins are of limited dimension such that they can, upon sufficient force, be moved out of the corresponding recesses and enclosure and, thus, permit cover to breakaway or release without further damage.

Figure 5:
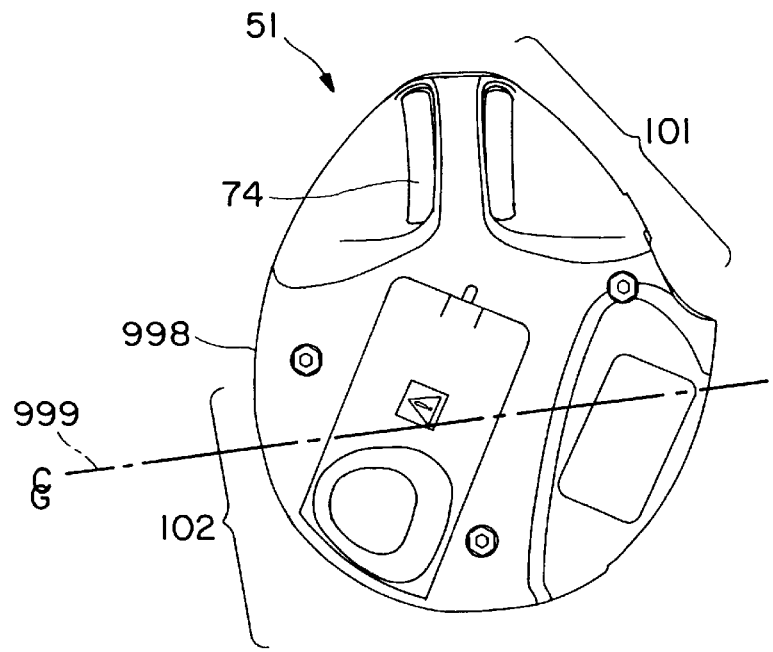
FIG. 5 is a back view of the recorder.

FIG. 5 is a back view of the recorder. As seen, recorder 51 features a belt loop 74 which may be used to mount the recorder to a patient using either the patient's belt or the shoulder strap. As also seen in this view, the device further features a unique weight distribution, particularly involving the device's batteries. As seen, the center of gravity 999 of the recorder taken within the major plane with the battery inserted is located below the widest portion of the recorder, generally designated as 998. This distribution of the weight below the case widest portion ensure the recorder hangs in a stable manner when worn. As best seen in FIG. 5 and also FIG. 6, the top portion 101 of the recorder is highly rounded, therby minimizing the patient's arms or fingers form catching on therecorder while being worn. As can be seen, the device has a partially elliptical cross section, when sectioned accross its features an at least partially elliptical cross section. The lower portion 102 is also rounded, albeit less than the top portion 101.

Figure 6:
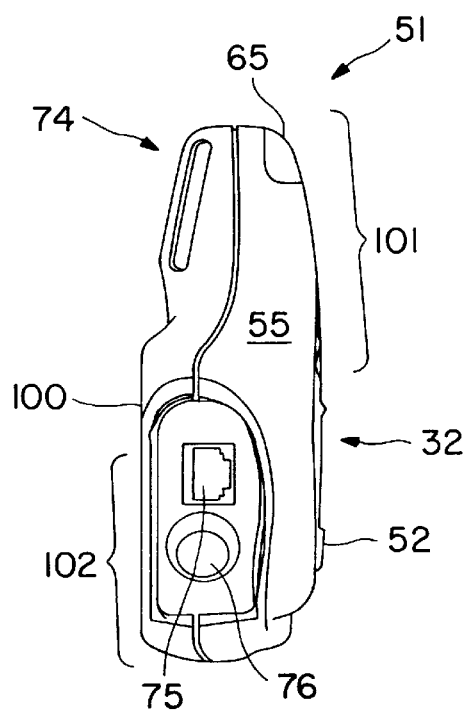
FIG. 6 is a side view of the recorder.

FIG. 6 is a side view of recorder 51. As further seen in this view, housing 55 features a pair of sensor inputs 75 and 76. In the preferred embodiment, input 75 is for a pH catheter while input 76 is for a pressure measuring catheter. As best seen in this view back portion of the recorder defines a flat plane 100 which corresponds and is opposite the control keypad 32 posiitoned beneath and covered by cover 52 in this view. Because plane 100 is flat and is directly opposite key pad, the the recorder may to be placed on a table top and have data entered through the keypad without the recorder rocking back and forth. The front portion of the recorder is also rounded. As further seen, recorder features an infra red lens 65 which permits an infrared link to a host be made using the IrD communication components shown in FIG. 2. As seen in this view lens is positioned along both an upper as well as a side surface of the recorder enclosure. This two sided or multi plane lens thereby permits a large degree of exposure to the internal IrD components inside the enclosure and thus permits an IrD link to be made with the recorder in a variety of positions, relative to the IrDA communication device 11 (referring to FIGS. 1A and 1B) Lens may be made of an known standard lens material. In the preferred embodiment lens is made of polycarbonate and enclosure itself, including cover, is fashioned from the polymer Crastin™ XMB 850 FR available from E.I. Du Pont De Nemours And Company, Wilmington, Del. The lens, however, should be formed so as to reach across both the upper side as well as front side of the recorder (referring once again to FIG. 6).

Figure 7:
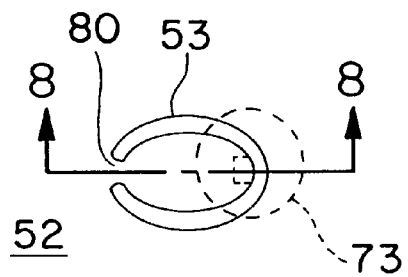
FIG. 7 is a detailed view of the movable push button shield.

FIG. 7 is a detailed view of the movable push button shield. As seen, movable push button shield 53 is designed to be positioned proximate the push button control 73, shown here as a dotted line. Shield is provided by cutting away the elongated section of cover such that a cantilevered strip remains. As seen, in the preferred embodiment, cantilever strip is somewhat oval in shape, although many or various types of shapes may also be used. The partial cutting away leaves the cantilever strip as a flexible hinge portion generally depicted here as 80 and permits the cantilever strip to open and thus be used to actuate push button.

Figure 8:
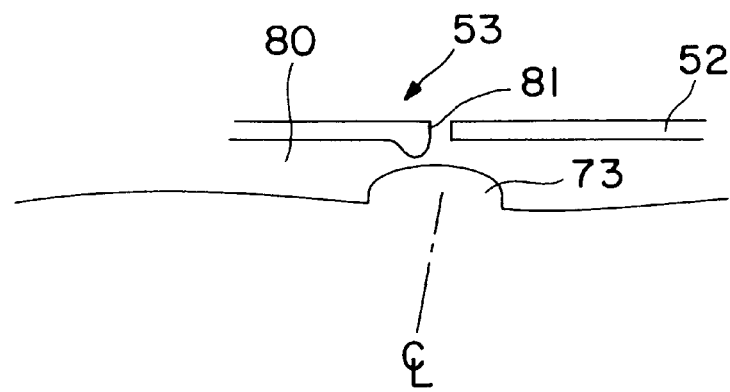
FIG. 8 is a sectional view of FIG. 7.

FIG. 8 is a sectional view of FIG. 7. As seen, cantilever section and the hinge which provides flexibility are disposed generally off-center from push button 73 such that the distal end of cantilever section 81 is shown in alignment with the center line of push button 73. Distal end further features a pronounced footing to further assist in the engagement of shield with push button and thus facilitate push button operation.

Figure 9:
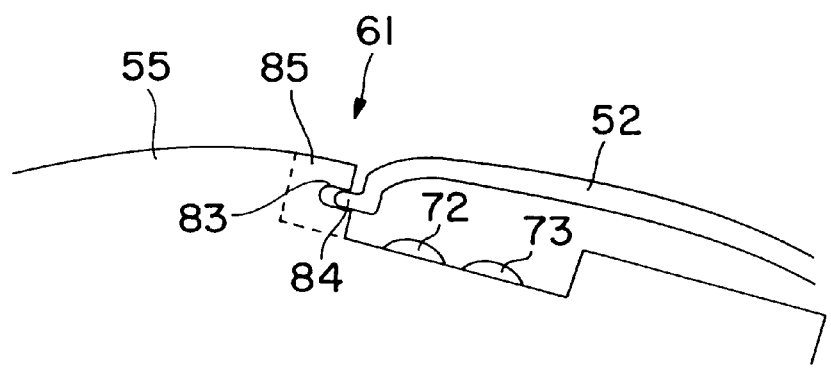
FIG. 9 is a detailed sectional view of catch.

FIG. 9 is a detailed sectional view of catch. As discussed above, cover may be only opened or closed through the release of a catch 61. As seen, catch features a recess 83 which co-operates with a finger 84 provided on cover 52. Because the cover is flexible, however, it may be deformed enough to disengage finger from recess.

As further seen in this FIG. 9 and also in FIG. 3, a trench 85 is provided in housing 55 to permit the engagement and, thus, removal of tongue from recess.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory recorder comprising:

a housing, the housing having a first control set, the control set featuring at least a first control and a second control;

a cover mounted to the housing, the cover moveable from a first position, in which the first control and the second control may be accessed, to a second position, in which only the first control may be accessed;

wherein the first control and the second control are push buttons;

further comprising the cover further having a movable push button shield;

wherein the push button shield comprises a lever integral with the cover, the lever defined by an elongated strip coupled to the cover only through an integral hinge.

2. An ambulatory recorder according to claim 1, wherein the integral hinge part is disposed off center from the first control.

3. An ambulatory recorder according to claim 1, the lever having a distal end, the distal end featuring a footing.

4. An ambulatory recorder comprising:

a housing, the housing having a first control set, the control set featuring at least a first control and a second control;

a cover mounted to the housing, the cover moveable from a first position, in which the first control and the second control may be accessed, to a second position, in which only the first control may be accessed, and means for sampling sensed physiologic data.

5. The ambulatory data recorder according to claim 4 wherein the means for sampling sensed physiologic data comprises a pH sensing catheter.

6. An ambulatory recorder comprising:

a housing, the housing having a first control set, the control set featuring at least a first control and a second control, and a display;

a cover mounted to the housing, the cover moveable from a first position, to a second position, the cover having a transparent portion and a opaque portion, the transparent position positioned so as to permit the display to be seen while the cover is in the second position;

wherein while the cover is in the first position the first control and the second control may be accessed, while in the second position only the first control may be accessed;

wherein the first control and the second control are push buttons;

further comprising the cover further having a moveable push button shield.

7. An ambulatory recorder according to claim 6, wherein the push button shield shields the first push button from view while permitting the first push button to be actuated.

8. An ambulatory recorder according to claim 7, wherein the push button shield is positioned above the first push button.

9. An ambulatory recorder according to claim 7, wherein the push button shield comprises a lever integral with the cover, the lever defined by an elongated strip coupled to the cover only through an integral hinge.

10. An ambulatory recorder according to claim 9, wherein the integral hinge part is disposed off center from the first control.

11. An ambulatory recorder according to claim 9, the lever having a distal end, the distal end featuring a footing.

12. An ambulatory recorder comprising:
   a housing, the housing having a first control set, the control set featuring at least a first control and a second control, and a display;
   a cover mounted to the housing, the cover moveable from a first position, to a second position, the cover having a transport portion and a opaque portion, the transparent position positioned so as to permit the display to be seen while the cover is in the second position;
   wherein while the cover is in the first position the first control and the second control may be accessed, while in the second position only the first control may be accessed;
   further comprising means for sampling sensed physiologic data.

13. The ambulatory data recorder according to claim 12, wherein the means for sampling the sensed physiologic data comprises a pH sensing catheter.

14. An ambulatory recorder comprising:
   a housing, the housing having a first control set, the control set featuring at least a first control and a second control, and a display;
   a cover mounted to the housing, the cover movable from a first position, to a second position, the cover having a transparent portion and a opaque portion, the transparent position positioned so as to permit the display to be seen while the cover is in the position;
   wherein while the cover is in the first position the first control and the second control may be accessed, while in the second position only the first control may be accessed;
   further comprising a mounting for mounting the ambulatory recorder to a patient.

15. The ambulatory data recorder according to claim 14, wherein the mounting comprises a loop configured for a belt or a shoulder strap to be inserted therethrough.

16. An ambulatory recorder comprising:
   a housing, the housing having a first control set, the control set featuring at least a first control and a second control, and a display;
   a cover mounted to the housings, the cover moveable from a first position, to a second position,
   wherein the housing further has a mounting for mounting the ambulatory recorder to a patient;
   wherein the first control and the second control are push buttons;
   further comprising the cover further having a moveable push button shield.

17. An ambulatory recorder according to claim 16, wherein the push button shield shields the first push button from view while permitting the first push button to be actuated.

18. An ambulatory recorder according to claim 17, wherein the push button shield is positioned above the first push button.

19. An ambulatory recorder according to claim 17, wherein the push button shield comprises a lever integral with the cover, the lever defined by an elongated strip coupled to the cover only through an integral hinge.

20. An ambulatory recorder according to claim 19, wherein the integral hinge part is disposed off center from the first control.

21. An ambulatory recorder according to claim 19, the lever having a distal end, the distal end featuring a footing.

22. An ambulatory recorder comprising:
   a housing, the housing having a first control set, the control set featuring at least a first control and a second control, and a display;
   a cover mounted to the housing, the cover moveable from a first position, to a second position,
   wherein the housing further has a mounting for mounting the ambulatory recorder to a patient;
   further comprising means for sampling the sensed physiologic data;
   wherein the means for sampling the sensed physiologic data comprises a pH sensing catheter.

* * * * *

UNITED STATES PATENT AND TRADEMARK OFFICE
CERTIFICATE OF CORRECTION

PATENT NO.     : 6,077,223
DATED          : June 20, 2000
INVENTOR(S)    : Satherley It is certified that error appears in the above-identified patent and that said Letters Patent is hereby corrected as shown below:

<u>Column 7,</u>
Line 37, change "in the position" to -- in the second position --.

Signed and Sealed this

Twenty-fifth Day of March, 2003

JAMES E. ROGAN
*Director of the United States Patent and Trademark Office*